Figure 1:
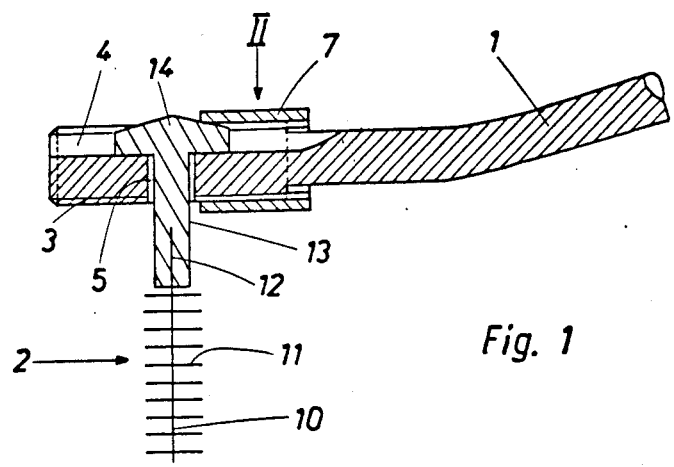

United States Patent [19]

Breitschmid

[11] Patent Number: 4,751,761
[45] Date of Patent: Jun. 21, 1988

[54] DEVICE FOR CLEANING INTERDENTAL SPACES

[75] Inventor: Ulrich Breitschmid, Meggen, Switzerland

[73] Assignee: Curaden AG., Kriens, Switzerland

[21] Appl. No.: 878,983

[22] PCT Filed: Oct. 1, 1985

[86] PCT No.: PCT/CH85/00141
§ 371 Date: Jun. 2, 1986
§ 102(e) Date: Jun. 2, 1986

[87] PCT Pub. No.: WO86/02532
PCT Pub. Date: May 9, 1986

[30] Foreign Application Priority Data

Oct. 25, 1984 [CH] Switzerland .................. 5108/84

[51] Int. Cl.$^4$ .................................................. A46B 9/04
[52] U.S. Cl. ........................................ 15/176; 15/194; 15/167.1
[58] Field of Search .............. 15/167 R, 176, 206, 15/191 R, 194, 145

[56] References Cited

U.S. PATENT DOCUMENTS

| | | | |
|---|---|---|---|
| 1,598,224 | 8/1926 | Van Sant | 15/167 R |
| 2,189,175 | 2/1940 | Jackson | 15/167 R |
| 2,624,062 | 1/1953 | Knoderer | 15/167 R |
| 3,559,226 | 2/1971 | Burns . | |
| 4,222,143 | 9/1980 | Tarrson et al. . | |
| 4,319,377 | 3/1982 | Tarrson et al. . | |

FOREIGN PATENT DOCUMENTS 0001044 3/1979 European Pat. Off. .

Primary Examiner—Peter Feldman
Attorney, Agent, or Firm—Brady, O'Boyle & Gates

[57] ABSTRACT

A dental brush (2) is held exchangeably at one end of a handle (1). The handle end has a bolt thread (3) on which is seated a threaded sleeve (7), along with a passage bore (5) extending transversely through the bolt thread, and longitudinal groove (4). The bristle carrier (10) of the brush (2) is seated in a cylindrical mounting (13) of a synthetic resin, a cross member (14) forming an abutment integrally formed therewith at the free end of this mounting. The brush (2) is inserted with the bristle (11) leading through the passage bore (5), the cross member (14) is introduced into the groove (4), and the threaded sleeve (7) is threaded on the bolt thread (4) over the cross member (14), the latter being clamped in place between the sleeve (7) and the bottom of the groove (4).

The mounting (13) provides a quick, effortless, and firm mounting of the brush (2) to the handle (1). Furthermore, thereby the danger of injuries caused by the free bristle carrier end (12) is avoided, and the bristle carrier (10) is protected against snapping off and breaking.

12 Claims, 2 Drawing Sheets

U.S. Patent    Jun. 21, 1988    Sheet 1 of 2    4,751,761

DEVICE FOR CLEANING INTERDENTAL SPACES

The invention relates to a device for cleaning the spaces between teeth.

The brushes utilized for the conventional devices of this type (U.S. Pat. Nos. 4,319,377 and 4,222,143) have a bristle carrier consisting of a twisted wire loop and exhibiting for mounting purposes an end member projecting out of the bristle body. This end member is extended, in the conventional devices, through a passage hole of the handle and bent over toward the handle whereupon a sleeve supported on the handle is pushed over the bent wire end. Bending over of the wire end and holding down of the bent wire end, which latter step is unavoidable during placement of the sleeve because of the spring-back action of the wire, are troublesome, and the wire end can cause injuries. In case the brush seizes between the teeth during interproximal cleaning, and a vigorous pull is exerted on the handle to release the brush, there is the danger that the wire breaks off at the edge of the passage hole.

Danger of breakage also exists during prolonged use of the brush, because the wire is flexed to and fro at the hole edge and is worn off. Removal of the broken-off brush sticking between the teeth is extremely difficult in such a case, and there is the hazard that the oral cavity is injured by the sharp, broken-off wire end.

The invention is based on the object of mounting the brush in a simple way, reliably and safe from breakage, at the handle, and avoiding the danger of injuries.

Due to the fact that the end of the bristle carrier, which latter usually consists of wire, is located in the molded part, the latter protects the user from injuries caused by the wire end. The molded part additionally protects the bristle carrier against being snapped off by bending and against breaking at the holding part of the handle. An object of the invention is to provide a structure that solves the task of preventing snapping or breaking off of the bristle carrier where it leads out of the molded part. In one form of the invention the molded part can be manufactured of a relatively hard synthetic resin wherein the bristle carrier is held more reliably than in a soft-elastic synthetic resin. In case of the latter, there is the danger that the bristle carrier, during use, will gradually work itself out of, or detach itself from, the synthetic resin.

Figure 2:
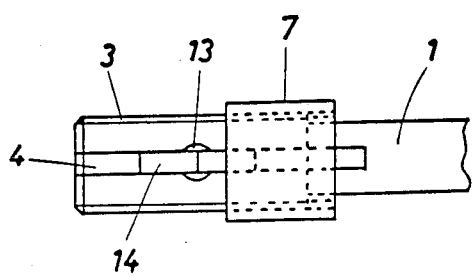
Figure 3:
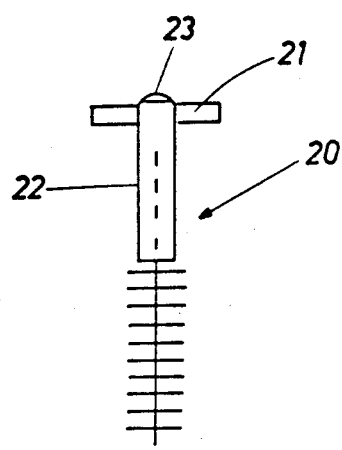
Figure 5:
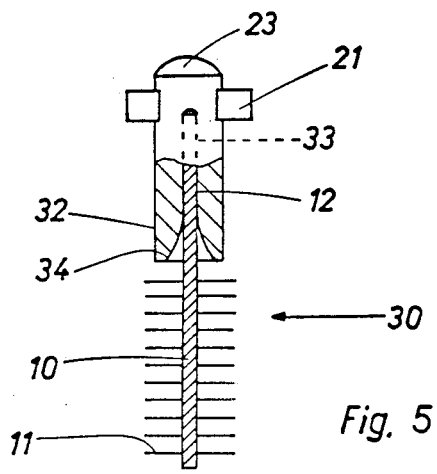
Figure 4:
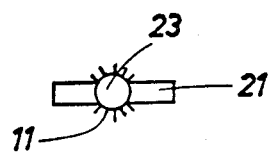
Figure 6:
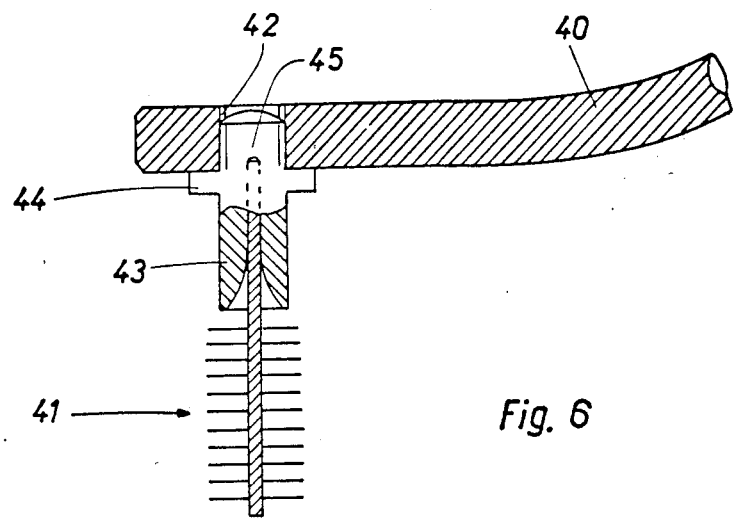
Figure 7:
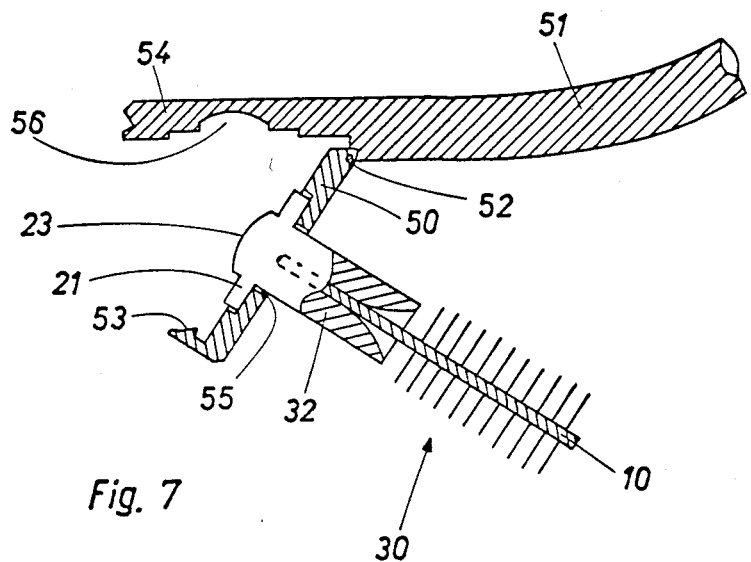

Embodiments of the invention will be described in greater detail below with reference to the drawing wherein:

FIG. 1 is a longitudinal section through a device for interproximal cleaning,

FIG. 2 is a top view of the device in the viewing direction of arrow II in FIG. 1, FIG. 3 is a lateral view of a modification of the brush of the device according to FIG. 1, FIG. 4 is a top view of the brush of FIG. 3, FIG. 5 is a lateral view, partially in section, of a preferred version of the brush of the device according to FIG. 1, FIG. 6 is a longitudinal section through a modification of the device of FIG. 1, and FIG. 7 shows a longitudinal section through another version of the device of FIG. 1.

The device illustrated in FIG. 1 comprises a stick-shaped handle 1 of which merely one end portion is shown, designed as a holder for an interdental brush (interproximal brush) 2. The illustrated handle end has a bolt thread 3 through which extend, in the axial direction, a groove 4 and, perpendicularly thereto, a passage bore 5, the diameter of the latter being larger than the width of the groove 4. A threaded sleeve 7 is threaded onto the bolt thread 3.

The brush 2 has a bristle carrier 10, formed in the usual way from a twisted wire loop, with bristles 11 and an end member 12 devoid of bristles. This end member 12 is cast into a cylindrical molded part 13 of a soft-elastic synthetic resin. A cross member 14, forming an abutment, is provided at the free end of the molded part 13, integrally with the latter, the two arms of this cross member tapering in a wedge shape toward the outside.

The diameter of the passage bore 5 is of a size adequate for being able to pass therethrough brushes 2 with the longest bristles 11 that can be considered for cleaning interproximal spaces. The diameter of the cylindrical molded part 13 is adapted, with a clearance, to the diameter of the passage bore 5 and the width of the cross member 14 is adapted, with a clearance, to the width of the groove 4. The thickness and wedge angle of the cross member arms are dimensioned so that the tapered ends of the cross member arms are still located within the groove, and the upper wedge surfaces gradually ascend out of the groove toward the top ridge line and form run-up surfaces for the sleeve 7.

The brush 2 is mounted to the handle 1 as follows: The molded part 13 is seized, and the brush is guided, with the bristles 11 leading—in FIG. 1 from above—through the bore 5, the cross member 14 sliding into the groove 4 and abutting against the floor of the latter. Thereupon, the threaded sleeve 7 is threaded along the bolt thread 3 in FIG. 1 toward the left, the sleeve thread running up on the upper wedge surface or run-up surface of the right arm of the cross member and this arm being clamped in place between the sleeve 7 and the bottom 4 of the groove.

The brush 20 illustrated in FIGS. 3 and 4 is likewise intended for mounting to the handle end illustrated in FIG. 1. This brush differs from the brush 2 by a differently configured cross member 21 of its molded part 22. The two arms of the cross member 21 have a constant thickness, adapted to the depth of the groove 4, and are molded integrally with the shell of the cylindrical molded part 22, the molded part exhibiting a curved head portion 23 projecting past the cross member. Once the molded part 22 has been inserted in the bore 5 and the cross member 21 has come into contact with the bottom of the groove 4, the curved head portion 23 projects out of the groove. During threading, the threaded sleeve 7 moves over the arm of the cross member 21 facing the sleeve and then abuts against the part of the mounting 22 projecting from the bore 5 at the bottom. During further threading of the sleeve 7, the lower portion of the molded part is somewhat compressed as well as bent at an angle, and the sleeve runs up against the curved head surface, the head 23 and the cross member 21 being clamped in place between the sleeve and the bottom of the groove 4.

As mentioned above, the molded part 13, 22 consists, in the above-described embodiments, of a soft-elastic (rubber-elastic) synthetic resin so that it can readily be flexed elastically. Thereby, the part acts as protection against kinking of the bristle carrier made of twisted wire. The end member 12 of the bristle carrier or, respectively, wire 10, seated in the molded part, can be of such a length, as indicated in FIG. 3, that it extends into the portion of the molded part 22 located within the passage bore 5. However, as shown in FIG. 1, this component is suitably made of a shorter dimension, namely so that its end has a spacing from the bore 5, i.e. the molded part 13 thus has a wire-free section projecting downwardly out of the bore 5. This section is flexible in correspondence with the elasticity of the synthetic resin and absorbs the bending forces acting on the bristle carrier during cleaning of the interdental spaces. Thereby the danger of snapping off of the bristle carrier by kinking is avoided. There is the danger, though, in case of the soft-elastic synthetic resin that the bristle carrier will work itself out of the synthetic resin during use.

This danger is precluded by the brush 30 shown in FIG. 5 wherein the molded part 32 is made of a relatively hard synthetic resin while yet avoiding reliably a snapping off or breaking of the bristle carrier 10. The molded part 32 differs from the above-described molded parts 13, 22 in that its space accommodating the end member 12 of the bristle carrier 10 devoid of bristles has a rearward, cylindrical section 33 and a frontal section 34 that flares conically or hyperbolically toward the outlet. The rearward section of the end member 12 is firmly embedded in the rearward, cylindrical section 33 of the bore; the forward section of the end member 12 is flexibly supported in the gradually widening section 34 of the bore, with a clearance increasing in the direction of the bristles 11. Accordingly, the forward section of the end member 12 can flex elastically within the bore section 34, the wall of the latter preventing bending past the limit of elasticity. On account of the increase in width of the bore section 34, which is continuous toward the outlet, a uniform bending stress is attained on the bristle carrier 10, and the danger of snapping off and breaking of the bristle carrier 10 at the outlet from the relatively hard molded part 32, which danger would otherwise exist, is overcome.

Another essential feature for avoiding injuries in the oral cavity resides in providing that the mounting or, respectively, the cross member projects from the groove to an only slight extent, and that, in any event, the projecting portion has no sharp edges or projections.

A further advantage in the described device is that the brush can be replaced without efforts and quickly. In this connection, it is possible to utilize selectively brushes having varying bristle length. In order to make it easier to differentiate among brushes of differing bristle lengths, the molded parts of the brushes can consist of differently dyed synthetic resin, i.e. each bristle length can be associated with a specific color.

The sleeve could be mounted, instead of being threadable, also merely displaceably on a cylindrical handle end. The threading feature, though, provides, of course, an essentially better clamping action of the sleeve and avoids the danger of slipping of the sleeve.

In the version illustrated in FIG. 6, the handle 40 has merely a threaded hole 42 for the shape-mating holding of the brush 41. The molded part 43 of the brush 41 differs from the molded part 32 of brush 30 by the feature that the cross member 44, forming the abutment, is arranged, rather than at the end, in a middle zone, and that the cylindrical head 45 of the molded part 43, projecting past the cross member 44, is equipped with an external thread, by means of which the molded part can be threaded into the threaded hole 42.

In the version of the device illustrated in FIG. 7, a lower end section 50 of the handle 51 is mounted to the handle to be pivotable about an articulation axle 52. The lower end section 50 can be secured, on the end face in opposition to the axle 52, to the upper end section 54, integrally formed with the handle, by means of a snap closure 53. The brush of this device corresponds to the brush 30 shown in FIG. 5. With the snap closure 53 being released and the lower end section 50 being folded down, this brush is passed through a passage bore 55 provided in this end section, the lower part of the cross member 21 being inserted in a groove provided therefor in the lower end section 50. The upper end section 54 has a recess 56 adapted to the head 23 and to the upper part of the cross member 21 of the molded part 32, these components engaging into this recess when the lower end section 50 is folded upwards. The cross member 21 is then held, with the snap closure 53 being snapped in place, between the upper and lower end sections 54, 50 in a shape-mating fashion, and thus protected against pressure and tensile stress of the bristle carrier 10.

In order to avoid the danger of unlocking of the snap closure 53 if a strong pull is exerted on the bristle carrier 10, the two end sections 50, 54 can also exhibit recesses of such a configuration that the molded part 32 or, respectively, its cross member 21 is held in a shape-mating fashion between the two end sections 50, 54 with the bristle carrier 10 extending in parallel to the axle 52 (i.e. perpendicularly to the plane of the drawing in FIG. 7). In this case, the passage bore 55 is eliminated, and the cross member 21 is dimensioned of sufficient width so that it projects to an adequate extent into the recesses of both end sections 50, 54, which recesses are adapted to respectively one-half the width of this cross member, and thus the latter is supported in both end sections 50, 54 against tensile stress and pressure acting on the bristle carrier 10.

In a further embodiment of the device, not shown, the cylindrical molded part has a peripheral channel for a spring clip designed in the manner of a Seeger ring. The handle end has a passage bore corresponding to FIG. 1 and two guide slots on the side, wherein the legs of the spring clip can be displaced. Manipulation of the spring clip, though, requires a certain skill, and, for releasing the spring clip, the latter must have a part projecting past the handle end, and this part can injure the mouth cavity in case of careless handling of the device.

The molded part of the brush could also be connected to the handle end in the manner of a bayonet catch, but handling of such catch also requires some skill on account of the small size of the components.

In all of the aforedescribed embodiments of the device, the molded part 13, 22, 32, 43 of the brush 2, 20, 30, 41 is held at the handle end in a shape-mating fashion, this form-locking action preventing displacement of the molded part in the longitudinal extension of the bristle carrier 10 due to tensile or compressive forces acting on the latter. Except for the embodiment of FIG. 6, the mounting of the handle providing shape-mating engagement consists of two parts, one of which (handle end with groove 4 in FIG. 1; upper end section 54 with recess 56 in FIG. 7) is integrally formed at the handle, and the other of which is supported at the handle to be displaceable (sleeve 7 in FIG. 1) or foldable (end section 50 in FIG. 7), so that it can be released from its shape-mating position for exchanging the brush. The bipartite design of the mounting, though structurally somewhat more expensive than the simple arrangement of the mounting as a threaded bore 42 in FIG. 6, overcomes the drawback of the latter, namely that, after longer-term usage, calcareous material, toothpaste residues, etc., can settle in the threads, making threading of the molded part of the brush finally impossible.

I claim:

1. A device for cleaning the interporximal spaces, comprising an interdental brush (2; 20; 30) and a handle (1) designed at one end for an exchangeable mounting of said brush, said brush (2; 20; 30) having a bristle carrier (10) with an end member (12) devoid of bristles and a molded part (13; 22; 32) wherein said end member (12) is embedded, said molded part having an end facing away from said bristle carrier (10), said molded part (13; 22; 32) having an abutment (14; 21) which is formed at the end facing away from said bristle carrier (10) and which projects transversely to the longitudinal extension of the bristle carrier (10), said handle (1) having at said one end a recess (4) with a bottom, and a passage bore (5) which extends through the bottom of the recess (4), said molded part (13; 22; 32) being adapted, with a clearance, to said bore (5), said abutment (14; 21) being adapted to be accommodated on the bottom of the recess (4) for securing said molded part (13; 22; 32) against tensile force from the bristle carrier (10), and a sleeve (7) rotatably and/or displaceably supported on said one end of said handle for releasable securing the molded part (13; 22; 32) with the abutment (14; 21) accommodated on the bottom of the recess (4) in a non-displaceable shape-mating fashion against pressure from said bristle carrier (10).

2. A device according to claim 1, including a bore (33, 34) in said molded part (32; 43) in which said end member (12) of the bristle carrier (10) devoid of bristles is embedded, said bore being widened (34) in a direction toward the part of the bristle carrier (10) exhibiting the bristles (11), so that the rearward section of the end member (12) facing away from the bristles (11) is firmly seated in the molded part (32; 43), and the forward section of the end member (12) facing the bristles (11) is flexible in the molded part (32; 43) with a clearance increasing in a direction toward the bristles (11).

3. A device according to claim 1, in which said abutment (14) or a head (23) on the molded part (13; 22; 32) projecting past the abutment (21) has an inclined or curved run-up surface for the sleeve (7) so that the abutment (14) or, respectively, the head (23) with the abutment (21) can be firmly clamped between the sleeve (7) and the bottom of the recess (4).

4. A device according to claim 1, in which said molded part (13; 22; 32) is longer than the passage bore (5) and preferably has a cylindrical shape.

5. A device for cleaning the interproximal spaces, comprising an interdental brush (2; 20; 30) and a handle (1) designed at one end for an exchangeable mounting of said brush, said brush (2; 20; 30) having a bristle carrier (10) with bristles (11) thereon and with an end member (12) devoid of bristles and a molded part (13; 22; 32) wherein said end member (12) is embedded, said molded part having an end facing away from said bristle carrier (10), said molded part (13; 22; 32) having an abutment (14; 21) which is formed at the end facing away from said bristle carrier (10) and which projects transversely to the longitudinal extension of the bristle carrier (10), said handle (1) having at said one end a groove (4) with a bottom, and a passage bore (5) which extends through the bottom of the groove (4), and which is of an adequately large dimension for passing therethrough said bristle carrier (10) with said bristles (11), said molded part (13; 22; 32) being adapted, with a clearance, to said bore (5), said abutment (14; 21) being adapted to be accommodated on the bottom of the groove (4) for securing said molded part (13; 22; 32) against tensile force from the bristle carrier (10), and a sleeve (7) rotatably and/or displaceably supported on said one end of said handle for releasable securing the molded part (13; 22; 32) with the abutment (14; 21) accommodated on the bottom of the groove (4) in a non-displaceable shape-mating fashion against pressure from said bristle carrier (10).

6. A device according to claim 5, in which said abutment is constituted by a cross member (14; 21).

7. A device according to claim 5, in which said molded part (13; 22; 32) consists of a soft-elastic synthetic resin.

8. A device according to claim 5, in which said end member (12) of the bristle carrirer (10) that is devoid of bristles is seated only in a portion of the molded part (13), and the remaining portion of the molded part (13) is longer than the passage bore (5).

9. A device according to claim 5, including a bore (33, 34) in said molded part (32; 43) in which said end member (12) of the bristle carrier (10) devoid of bristles is embedded, said bore being widened (34) in a direction toward the part of the bristle carrier (10) exhibiting the bristles (11), so that the rearward section of the end member (12) facing away from the bristles (11) is firmly seated in the molded part (32; 43), and the forward section of the end member (12) facing the bristles (11) is flexible in the molded part (32; 43) with a clearance increasing in a direction toward the bristles (11).

10. A device according to claim 5, in which said abutment (14) or a head (23) on the molded part (13; 22; 32) projecting pass the abutment (21) has an inclined or curved run-up surface for the sleeve (7) so that the abutment (14) or, respectively, the head (23) with the abutment (21) can be firmly clamped between the sleeve (7) and the bottom of the groove (4).

11. A device according to claim 5, in which said molded part (13; 22; 32) is longer than the passage bore (5) and preferably has a cylindrical shape.

12. A device for cleaning the interproximal spaces, comprising an interdental brush (30) and a handle (51), said brush (30) having a bristle carrier (10) with bristles (11) thereon and with an end member (12) devoid of bristles and a molded part (32) wherein said end member (12) is embedded, said molded part having an end facing away from said bristle carrier (10), said handle (51) having at one end a mounting (50, 54) for an exchangeable mounting of said molded part (32), said molded part (32) having an abutment (21) which is formed at the end facing away from said bristle carrier (10) and which projects transversely to the longitudinal extension of the bristle carrier (10), said mounting (50, 54) having two sections (50, 54) for securing said molded part (32) with said abutment (21) in a shape-mating fashion against tensile force and pressure from said bristle carrier (10), one of said sections (54) being formed integrally with said handle (51), and the other of said sections (50) consisting of a part (50) pivotally (52) mounted at said handle (51) and securable in the shape-mating position by means of a snap closure (53) at the handle (51), and releasable by said snap closure from its shape-mating position for exchanging the brush (30), a passage bore (55) being provided in one or the other of said two section (50, 54), the bore (55) being dimensioned of a size sufficient for passing said bristle carrier (10) with said bristles (11) therethrough, and said molded part (32) being adapted with clearance to said bore (55).

* * * * *